United States Patent [19]

Clarkson, Jr. et al.

[11] 4,136,198

[45] Jan. 23, 1979

[54] METHOD FOR THE CONTROL OF TRYPANOSOMIASIS

[75] Inventors: Allen B. Clarkson, Jr.; Fredrick H. Brohn, both of New York, N.Y.

[73] Assignee: The Rockefeller University, New York, N.Y.

[21] Appl. No.: 714,156

[22] Filed: Aug. 13, 1976

[51] Int. Cl.$^2$ .............................................. A61K 31/16
[52] U.S. Cl. ................................................... 424/320
[58] Field of Search ........................................ 424/320

[56] References Cited

PUBLICATIONS

Chemical Abstracts 74: 83062y (1971).
Osol Farrar, Dispensatory of the USA, 25th Ed., Part I, 1955, pp. 611–613.
Chemical Abstracts 63: 18966(d), (1965).
Chemical Abstracts 65: 6231(g), (1966).

Primary Examiner—Jerome D. Goldberg
Attorney, Agent, or Firm—Oblon, Fisher, Spivak, McClelland & Maier

[57] ABSTRACT

A composition comprising from 0.02 to 17 parts by weight of glycerol per part by weight of an iron chelating agent selected from the group consisting of salicyl hydroxyamic acid; 2,3- and 3,4-dihydroxy benzoic acid; and halobenzohydroxamic; e.g., m-iodobenzohydroxamic acid and m-chlorobenzohydroxamic acid; as well as their $C_1$ to $C_4$ alkyl esters. When this composition is administered parenterally, it is found to block aerobic and anaerobic glucose catabolism and thereby accomplish control of several trypanosomes, including *Trypanosoma brucei, T. gambiensi, T. rhodesiensi, T. equiperdum, T. evansi, T. congolense* and *T. vivax*. In mammals, the therapeutic dosage is calculated to provide at least 138 mg/kg of body weight of glycerol and at least 96 mg/kg of body weight of the iron chelating agent.

2 Claims, No Drawings

METHOD FOR THE CONTROL OF TRYPANOSOMIASIS

The invention described herein was made in the course of work under a grant or an award from the Department of Health, Education and Welfare.

SUMMARY OF THE INVENTION

This invention relates to novel compositions comprising an admixture of glycerol and one or more selected iron chelating agents. In particular, this invention relates to compositions comprising glycerol and the iron chelating agent salicyl hydroxamic acid (SHAM). These novel compositions have antiparasitic activity and are particularly active against trypanasomes including *Trypanosoma brucei, T. gambiensi, T. rhodesiensi, T. equiperdum and T. evansi.* This invention in particular relates to novel methods for the therapeutic control of Trypanosoma infections in mammals.

Thus, a primary object of this invention is to provide a means for the control of trypanosomiasis. This disease is caused by infection with parasites of the genus Trypanosoma.

Trypanosomiasis is a debilitating often fatal parasitic disease which occurs in the so-called tsetse fly belt of Africa which straddles the rain forests and extends northward to the dry areas of the Sahara and southward to Zambia, and nearby South Africa, Botswana and Angola.

The disease is introduced into the bloodstream of a susceptible mammalian host by various intermediate carriers. The most common carrier is the tsetse fly. Efforts to control the disease have so far not proven completely effective.

Although control of the carrier by employing insecticides has been attempted, the vast area where the disease is endemic militates against the success of this control measure. Likewise control by chemotherapeutic means has so far met with only moderate success, in part because of increasing resistance to chemotherapy on the part of the various trypanosomes.

Trypanosomiasis is the major inhibitor for the development of the most potentially productive areas of Africa. Not only is trypanosomiasis a direct threat to man, but it also affects cattle and prevents the development of vigorous cattle herds in the otherwise lush grasslands of the tsetse fly belt. Cattle could, absent the threat of this disease, provide an efficient protein source when grazed on the abundant grassland.

DESCRIPTION OF THE INVENTION

The novel composition of this invention comprises from 0.02 to 17 parts by weight glycerol for each part by weight of one or more iron chelating agents selected from the group consisting of salicyl hydroxamic acid; 2,3- and 3,4-dihydroxy benzoic acid and $C_1$ to $C_4$ alkyl esters thereof; halobenzohdroxamic acid, e.g., m-iodobenzohydroxamic acid and m-chlorobenzohydroxamic acid. As used herein, the term "halo" includes bromo, chloro and iodo. A preferred iron chelating agent is salicyl hydroxamic acid.

Also included within the instant invention are the pharmaceutically acceptable salts of the iron chelating agents.

The novel compositions are useful as antiparasitic agents, and are preferably employed in the treatment of trypanosomiasis in mammals. When so employed, the compositions can be combined with other non-toxic, pharmaceutically acceptable carriers.

The administered dose may comprise from 0.01 to 100% by weight of the active composition, the remainder being carrier or other inert substances. The dosage form is administered at levels of from 138 to 1656 mg/kg of body weight for glycerol and 96 to 573 mg/kg body weight iron chelate per day. The particular individual dosage is a function of factors such as age, weight, degree of infection. In general, a preferred dosage range is from 138 to 276 mg/kg of body weight for glycerol and 96 to 191 mg/kg for the iron chelate.

When the composition of this invention is administered parenterally, it is found to block aerobic and anaerobic glucose catabolism. The preferred route of administration is intravenous, although intraperitoneal routes are satisfactory. It should be noted that the threshold effective does of glycerol is 138 mg/kg and of iron chelating agent is 48 mg/kg. Therefore, it should be ascertained that the quantity of each component in the composition meet the minimum dosage level. Further, it is contemplated that in many infections, a single dose will be insufficient and repeated dosages will be required.

In addition, administration can also be performed concomitantly with other therapeutic agents active against trypanosomes or other infectious agents commonly encountered in conjunction with trypanosomes.

In preparing the composition of this invention, the glycerol is admixed with the iron chelating agent to form a homogeneous mixture, whether a solution, suspension, or emulsion by techniques well known in the art.

We claim:

1. A method of combatting trypanosomiasis comprising administering parenterally to an infected host a composition comprising 138 to 276 mg/kg body weight of glycerol and from 96 to 191 mg/kg of an iron chelating agent selected from the group consisting of halobenzohydroxamic acid, and pharmaceutically acceptable salts thereof, per day.

2. The method of claim 1, wherein the composition administered comprises at least 96 mg/kg body weight of the halobenzohydroxamic acid compound and at least 138 mg/Kg body weight of the glycerol.